United States Patent [19]

Luo

[11] Patent Number: 4,626,276

[45] Date of Patent: Dec. 2, 1986

[54] HERBICIDAL TRANS-2-[(3-CHLOROALLYLOX-YIMINO)ALKYL]-5-(SUBSTITUTEDSUL-FINYLALKYL)-CYCLOHEXANE-1,3-DIONES AND DERIVATIVES THEREOF

[75] Inventor: Tatao Luo, El Sobrante, Calif.

[73] Assignee: Chevron Research Company, San Francisco, Calif.

[21] Appl. No.: 834,707

[22] Filed: Feb. 28, 1986

Related U.S. Application Data

[63] Continuation-in-part of Ser. No. 618,979, Jun. 11, 1984, abandoned.

[51] Int. Cl.$^4$ .................... C07C 147/14; A01N 31/04
[52] U.S. Cl. .......................................... 71/103; 560/8; 560/100; 560/105; 560/106; 560/107; 560/252; 564/256
[58] Field of Search ............... 560/100, 105, 106, 107, 560/252, 8; 564/256; 71/103

[56] References Cited

U.S. PATENT DOCUMENTS

| | | | |
|---|---|---|---|
| 3,820,975 | 6/1974 | Poje | 71/98 |
| 3,943,176 | 3/1976 | Dunbar | 71/103 |
| 3,989,737 | 11/1976 | Sawaki | 560/125 |
| 4,249,937 | 2/1981 | Iwataki | 71/103 |
| 4,427,440 | 1/1984 | Osten | 71/103 |
| 4,440,566 | 4/1984 | Luo | 560/125 |
| 4,515,729 | 5/1985 | Iwataki | 71/103 |

FOREIGN PATENT DOCUMENTS

| | | |
|---|---|---|
| 891190 | 6/1981 | Belgium . |
| 891413 | 6/1981 | Belgium . |
| 46860 | 3/1982 | European Pat. Off. . |
| 3227332 | 1/1984 | Fed. Rep. of Germany . |
| 3227389 | 1/1984 | Fed. Rep. of Germany . |
| 55-28957 | 2/1980 | Japan ...... 71/103 |
| 55-89203 | 7/1980 | Japan ...... 71/103 |
| 55-115802 | 9/1980 | Japan ...... 71/103 |

*Primary Examiner*—Michael L. Shippen
*Attorney, Agent, or Firm*—T. G. DeJonghe; L. S. Squires

[57] ABSTRACT

Herbicidal trans-2-[(3-chloroallyloxyimino)alkyl]-5-(substitutedsulfinylalkyl)-cyclohexane-1,3-diones and derivatives thereof. The compounds can be prepared via oxidation of the corresponding 5-(substitutedthioalkyl) precursors. The compounds are especially useful as selective herbicides active against grassy weeds.

26 Claims, No Drawings

HERBICIDAL TRANS-2-[(3-CHLOROALLYLOXYIMINO)AL-KYL]-5-(SUBSTITUTEDSULFINYLALKYL)-CYCLOHEXANE-1,3-DIONES AND DERIVATIVES THEREOF

CROSS-REFERENCE TO RELATED APPLICATION

This application is a continuation-in-part of application Ser. No. 618,979, filed June 11, 1984, now abandoned.

BACKGROUND OF THE INVENTION

This invention relates to trans-2-[(3-chloroallyloxyimino)alkyl]-5-(substitutedsulfinyl-alkyl) cyclohexane-1,3-diones and to the use of such compounds as herbicides, especially against grassy weeds, and plant growth regulators.

A number of 2-substituted iminoalkyl 5-substituted cyclohexane 1,3-diones are described in U.S. Pats. Nos. 3,943,176; 3,989,737; 3,950,420; 4,011,256; 4,033,754; 4,249,937; published European Patent Application No. 46860 and published German Patent Application No. 3,219,315.

My Belgian Patent No. 891,190, issued 1981, discloses herbicidal cis and trans-2-[(3-chloroallyloxyimino)alkyl]-5-(alkyl, alkylthio, and alkylthioalkyl) cyclohexane 1,3-diones and derivatives thereof. My Belgian patent 897,413 and my U.S. Pat. No. 4,440,556 disclose trans-2[1-(3-chloroallyloxyimino)butyl]-5-(2ethylthiopropyl) cyclohexane 1,3-dione as a selective grassy weed herbicide having improved soil stability.

German Patent applications DE No. 3,227,332 and 3,227,389 laid open Jan. 26, 1984, disclose herbicidal 2-[optionally halogen substituted alkyl, alkenyl or alkenyl)iminoalkyl] cyclohexane 1,3-diones, respectively, having a 5-position ring substituent defined as a $C_1$ to $C_{10}$ alkyl group substituted in the chain with 2 to 4 of the heteroatoms O and/or S or —S(O)— or —SO$_2$— and —R$^3$S(O)$_n$R$^4$ wherein n is 0, 1 or 2, R$^3$ is alkylene and R$^4$ is certain optionally substituted alkenyl, alkynyl, aryl, arylalkyl, or arylalkenyl groups.

SUMMARY OF THE INVENTION

The present invention provides selective herbicidal compounds having excellent pre-emergence and post-emergence phytotoxic activity against grasses. Moreover, the compounds exhibit exceptional soil stability and long term residual pre-emergent phytotoxicity against grassy weeds. The compounds primarily exhibit selective phytotoxicity against grasses and generally can be safely applied to control grassy weeds in broadleaf crops. At lower dosages the compounds also exhibit plant growth regulating activity, but are primarily excellent selective grass herbicides with long term residual phytotoxicity and good crop safety.

The compounds of the present invention can be represented by the following generic formula:

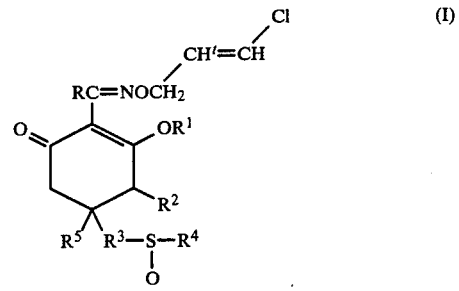

wherein R is lower alkyl having 1 through 6 carbon atoms; $R^1$ is hydrogen, a compatible cation, or the group

wherein $R^6$ is lower alkyl having 1 through 6 carbon atoms, phenyl, indenyl, naphthyl or benzyl;

$R^2$ is hydrogen, carboxy or alkoxycarbonyl having 2 through 6 carbon atoms;

$R^3$ is lower alkylene having 1 through 6 carbon atoms and includes both straight chain and branched chain alkylene groups.

$R^4$ lower alkyl having 1 through 6 carbon atoms phenyl or substituted phenyl having 1 through 3 substituents independently selected from the group of lower alkyl, lower alkoxy, halo, and lower haloalkyl having 1 through 4 carbon atoms and 1 through 3 of the same or different halo atoms; and $R^5$ is hydrogen or lower alkyl; and the double bond designation t indicates the compound is trans geometrically oriented with respect to the double bond.

The compounds of Formula (I) wherein $R^1$ is hydrogen exist as keto⇌enol tautermers. The compounds also have two or more asymmetric carbon atoms and can exist as optical isomers. In some instances the compounds also exist as geometric isomers. The above formula is intended to encompass the respective individual isomers as well as mixtures thereof and the respective isomers as well as mixtures thereof are encompassed within the invention.

In a further aspect, the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, especially grassy weeds, which comprises treating the growth medium and/or the foliage of such vegetation with a herbicidally effective amount of the compound(s) of Formula (I) and/or compatible salts thereof.

In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 1 and 2 set forth hereinbelow on pages 13 and 15. In terms of substituents, the preferred compounds are those wherein R is lower alkyl having 2 through 4 carbon atoms and especially propyl. $R^1$ is preferably hydrogen, a cation, lower alkanoyl or benzoyl and more preferably, hydrogen or a cation. $R^2$ is preferably hydrogen. $R^3$ is preferably a branched alkylene having 2 through 4 carbon atoms and more preferably —$CH_2CH(CH_3)$—. $R^4$ is preferably alkyl having 2 through 4 carbon atoms, phenyl, monosubstituted phenyl (e.g. 4-chlorophenyl, 4-bromophenyl) or disubstituted phenyl. $R^5$ is preferably lower alkyl having 1 through 4 carbon atoms or more preferably is hydrogen. More preferably, the group —$R^3S$—$R^4$ is —$CH_2CH(CH_3)S(O)CH_2CH_3$ and $R^5$ is hydrogen. The preferred compounds have at least one preferred substituent and more preferably have a combination of two or more preferred substituents. I have found that the compound trans-2-[1-(3-chloroalkyloxyimino)butyl]-5-(2-ethylsulfinylpropyl) cyclohexane 1,3-dione (i.e., named as the keto-tautomer) exhibits an exceptionally superior combination of grassy weed phytotoxicity, crop safety and residual long term grassy weed preemergence phytotoxicity.

The compounds of the present invention can be prepared via oxidation of the corresponding 5-alkylthioalkylene analogs. This can be schematically represented by the overall reaction equation:

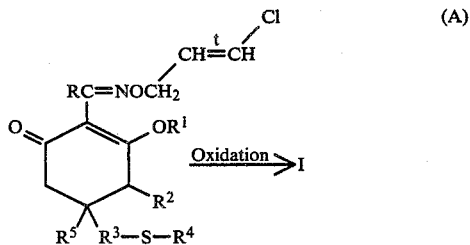

wherein R, $R^1$, $R^2$, $R^3$, $R^4$, $R^5$ and $t$ are as defined hereinabove.

The oxidation can be effected via any suitable oxidation procedure. For example, the oxidation can be effected by contacting the compound of Formula A with an oxidation agent preferably in an inert organic solvent. Typically, this is conducted at temperatures in the range of about from 0° C. to 80° C., preferably 10° C. to 40° C., for about from 1 to 24 hours, preferably 4 to 10 hours using about from 1 to 3 mole equivalent of oxidizing agent per mole of compound A. Suitable inert organic solvents which can be used include, for example, acetone, methylene chloride, and the like and compatible mixtures thereof. Suitable oxidizing agents which can be used include, for example, hydrogen peroxide, m-chloroperbenzoic acid, and the like.

In conducting the oxidation, care should be taken to prevent or minimize oxidation to the sulfonyl analog. As I have found, the sulfinyl compounds of the present invention are superior selective herbicides over their corresponding sulfonyl analog. Good results can be obtained using about a 10 to 30 wt. % hydrogen peroxidewater solution as the oxidizing agent.

The compounds of Formula A are generally known compounds and described in U.S. Pat. No. 4,440,566. The compounds of Formula A and can be prepared by known procedures or obvious modifications thereof using the appropriate or appropriately substituted reactants.

The salts of Formula I (i.e., wherein $R^1$ is a cation) can be prepared by treating the corresponding 1,3-dione compounds of Formula I (i.e. $R^1$ is hydrogen) with a base or metal halide via conventional procedures. Additional variation in the cations can be effected via ion exchange with an ion exchange resin having the desired cation.

General Process Conditions

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary.

The term "lower alkyl" refers to both straight-and branched-chain alkyl groups having a total of from 1 through 6 carbon atoms preferably 1 through 4 carbon atoms and includes primary, secondary and tertiary alkyl groups. Typical lower alkyls include, for example, methyl, ethyl, n-propyl, isopropyl, n-butyl, t-butyl.

The term "lower alkylene" refers to both straight chained and branched chained alkylene groups having 1 through 6 carbon atoms, preferably 1 through 4 carbon atoms and includes, for example, —CH₂—; —CH₂—CH₂—;

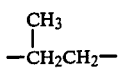

and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group —OR' wherein R' is lower alkyl.

The term "lower alkylthio" refers to the group —SR' wherein R' is lower alkyl.

The term "lower alkoxyalkyl" refers to the group R'OR''— wherein R' and R'' are independently straight chain or branched chain alkyl groups having 1 through 3 carbon atoms.

The term "alkylthioalkyl" refers to the group R'SR''— wherein R' and R'' are independently straight chain or branched chain alkyl groups.

The term "lower alkoxycarbonyl" refers to the group

wherein R' is lower alkyl and can be straight or branched chained. Typical alkoxycarbonylalkyl groups include for example, methoxycarbonyl, ethoxycarbonyl, t-butylcarbonyl, hexoxycarbonyl, and the like.

The term "halo" refers to the group of fluoro, chloro, bromo and iodo.

The term "lower haloalkyl" refers to haloalkyl compounds having 1 through 4 carbon atoms and 1 through 3 halo atoms independently selected from the group of fluoro, chloro, bromo and iodo. Preferably the lower haloalkyl group has 1 or 2 carbon atoms and more preferably is trifluoromethyl.

The term "alkylsulfinylalkyl" refers to the group having the formula

wherein R' and R'' are independently straight chain or branched chain alkyl groups.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "monosubstituted phenyl" refers to substituted phenyls having only one substituent, for example, 2-bromophenyl, 3-chlorophenyl, 4-trifluoromethylphenyl, and the like.

The term "disubstituted phenyl" refers to substituted phenyls having two substituents, for example, 2,6-dimethylphenyl, 3,5-dichlorophenyl, 2-ethyl-3-methoxyphenyl, and the like.

The term "compatible salts" or "cation" as used with respect to R¹ of Formula I, refers to salts which do not significantly adversely alter the herbicidal properties of the parent compound. Suitable salts include cation salts such as, for example, the cation salts of lithium, sodium, potassium, alkali earth metals, copper, zinc, magnesium ammonia, quaternary ammonium salts, and the like.

The term "room temperature" or "ambient temperature" refers to about 20°–25° C.

Utility

The compounds of Formula (I) exhibit both pre-emergence and post-emergence herbicidal activity against grassy weeds and exhibit especially good pre-emergence herbicidal activity. The compounds also exhibit good crop safety and long term pre-emergent phytotoxicity against grassy weeds.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability. The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Examples. Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, protonmagnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

EXAMPLE 1

Trans-2-[1-(3-chloroallyloxyimino)butyl]-5-(2-ethylsulfinylpropyl) cyclohexane 1,3-dione In this example, a mixture containing 2.2 g of trans-2-[1-(3-chloroallyloxyimino)butyl]-5-(2-ethylthiopropyl) cyclohexane 1,3-dione and 1 ml of aqueous 30% hydrogen peroxide in 10 ml of acetone was stirred at room temperature for about 2½ days and then concentrated by evaporation. The residue was mixed with 50 ml of ethyl ether, washed with 30 ml of saturated aqueous sodium bicarbonate solution, then washed with 30 ml of water, dried over magnesium sulfate and evaporated to dryness affording 1.9 g of the title compound.

Similarly, by applying the same procedure using the corresponding thio starting materials, the following compounds can be prepared:

Trans-2-[1-(3-chloroallyloxyimino)butyl]-3-acetyloxy-5-(2-ethylsulfinylpropyl)-cyclohex-2-ene-1-one;

trans-2-[1-(3-chloroallyloxyimino)butyl]-acetyloxy-4-methoxycarbonyl-5-(2-ethylsulfinylpropyl)-cyclohex-2-ene-1-one;

trans-2-[1-(3-chloroallyloxyimino)propyl]-5-(2-ethylsulfinylpropyl)-cyclohexane 1,3-dione;

3-sodium salt of trans-2-[1-(3-chloroallyloxyimino)butyl]-5-(2-ethylsulfinylpropyl)-cyclohexane 1,3-dione;

trans-2-[1-(3-chloroallyloxyimino)butyl]-5-methyl-5-(2-ethylsulfinylpropyl)-cyclohexane 1,3-dione;

trans-2-[1-(3-chloroallyloxyimino)butyl]-5-(2-ethylsulfinylethyl)-cyclohexane 1,3-dione;

trans-2-[1-(3-chloroallyloxyimino)butyl]-5-(2-propylsulfinylpropyl)-cyclohexane 1,3-dione;

trans-2-[1-(3-chloroallyloxyimino)butyl]-5-(6-hexylsulfinylhexyl)-cyclohexane 1,3-dione;

trans-2-[1-(3-chloroallyloxyimino)butyl]-5-(4-propylsulfinylbutyl)-cyclohexane 1,3-dione;

trans-2-[1-(3-chloroallyloxyimino)butyl]-5-(ethylsulfinylmethylene)-cyclohexane 1,3-dione;

trans-2-[1-(3-chloroallyloxyimino)butyl]-5-(2-t-butylsulfinylethyl)-cyclohexane 1,3-dione;

trans-2-[1-(3-chloroallyloxyimino)butyl]-5-isopropyl-5-(3-ethylsulfinylpropyl)-cyclohexane 1,3-dione;

trans-2-[1-(2-chloroallyloxyimino)propyl]-3-naphth-1-ylcarbonyloxy-5-(2-ethylsulfinylpropyl)-cyclohexane 1,3-dione;

trans-2-[1-(3-chloroallyloxyimino)butyl]-3-acetyloxy-5-(2-phenylsulfinylpropyl)cyclohex-2-ene-1-one;

trans-2-[1-(3-chloroallyloxyimino)butyl]-acetyloxy-4-methoxycarbonyl-5-[2-(2-fluorophenyl-sulfinyl)-propyl]-cyclohex-2-ene-1-one;

trans-2-[1-(3-chloroallyloxyimino)butyl]-5-[2-(4-chlorophenyl-sulfinyl)propyl]-cyclohexane 1,3-dione;

3-potassium salt of trans-2-[1-(3-chloroallyloxyimino)butyl]-5-(2-phenylsulfinylpropyl)-cyclohexane 1,3-dione;

trans-2-[1-(3-chloroallyloxyimino)butyl]-5-[2-(4-bromophenylsulfinyl)propyl]-cyclohexane 1,3-dione;

trans-2-[1-(3-chloroallyloxyimino)butyl]-5-methyl-5-[2-(2,6-dimethylphenylsulfinyl)propyl]-cyclohexane 1,3-dione;

trans-2-[1-(3-chloroallyloxyimino)butyl]-5-[2-(4trifluoromethylphenylsulfinyl)ethyl]-cyclohexane 1,3-dione;

trans-2-[1-(3-chloroallyloxyimino)-2-methylbutyl]-5-[2-(2-chloro-4-trifluoromethylphenylsulfinyl)propyl]-cyclohexane 1,3-dione;

trans-2-[1-(3-chloroallyloxyimino)butyl]-5-[6-(3-methoxyphenylsulfinyl)hexyl]-cyclohexane 1,3-dione;

trans-2-[1-(3-chloroallyloxyimino)ethyl]-5-[3-(3,5-dichlorophenylsulfinyl)butyl]-cyclohexane 1,3-dione;

trans-2-[1-(3-chloroallyloxyimino)butyl]-5-(2,4,5-trifluorophenylsulfinylmethylene)-cyclohexane 1,3-dione;

trans-2-[1-(3-chloroallyloxyimino)pentyl]-5-[2-methoxyphenylsulfinyl)ethyl]-cyclohexane 1,3-dione;

trans-2-[1-(3-chloroallyloxyimino)hexyl]-5-isopropyl-5-[3-(2,6-dimethyl-4-fluorophenyl)sulfinylpropyl]-cyclohexane 1,3-dione; and trans-2-[1-(3-chloroallyloxyimino)propyl]-3-benzoyloxy-5-(2-phenylsulfinylpropyl)-cyclohex-2-en-1-one.

EXAMPLE 2

The compounds listed in Table A hereinbelow were prepared using the appropriate starting materials and applying the procedure described in Example 1 hereinabove.

TABLE A

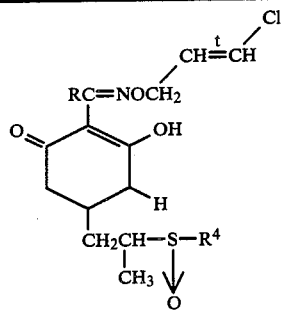

| | | | ELEMENTAL ANALYSIS | | | | | Melting |
| | | | Carbon | | Hydrogen | | Nitrogen | Point |
| No. | R | $R^4$ | Calc. | Found | Calc. | Found | Calc. | Found | °C. |
|---|---|---|---|---|---|---|---|---|---|
| 1 | $C_3H_7$ | $-C_2H_5$ | 55.44 | 53.68 | 7.24 | 6.74 | 3.59 | 3.98 | oil |
| 2 | $C_3H_7$ | $-C(CH_3)_3$ | 57.47 | 55.74 | 7.72 | 7.75 | 3.35 | 3.31 | oil |
| 3 | $C_3H_7$ | $-(CH_2)_3CH_3$ | 57.5 | 56 | 7.70 | 7.99 | 3.4 | 3.01 | oil |
| 4 | $C_3H_7$ | —cyclohexyl | 59.5 | 60.18 | 7.7 | 9.64 | 3.16 | 4.27 | oil |
| 5 | $C_3H_7$ | $CH(CH_3)_2$ | 56.5 | 57.16 | 7.4 | 8.76 | 3.5 | 3.99 | oil |
| 6 | $C_3H_7$ | $4\text{-Cl}\phi^*$ | 55.9 | 54.12 | 5.7 | 5.67 | 2.97 | 2.72 | oil |
| 7 | | | | | | | | | |
| 8 | | | | | | | | | |
| 9 | | | | | | | | | |
| 10 | | | | | | | | | |

$\phi^*$ = Phenyl, for example, 4-Cl$\phi$ = 4-chlorophenyl

EXAMPLE 3

In this example, compounds Nos. 1 and 2 of Table A were respectively tested using the procedures described hereinbelow for pre-emergent and post-emergent activity against a variety of grasses and broad-leaf plants including one grain crop and one broad-leaf crop. The compounds tested are identified by compound number in Table A hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface either at a dose of 27.5 micrograms/cm² or in some instances as indicated in Table 1 hereinbelow, certain of the compounds were tested at a lower dosage of 15.6 micrograms/cm². The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm². After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1

Pre-Emergence Herbicidal Activity
Application Rate: 27.5 micrograms/cm², unless otherwise noted

| | Broad-Leaf Plants % Phytotoxicity | | | | Grasses % Phytotoxicity | | | |
|---|---|---|---|---|---|---|---|---|
| Compound No. | Lambs-quarter | Mustard | Pig-weed | Soybean | Crab-grass | Water-grass | Wild Oats | Rice |
| 1 | 0 | 0 | 0 | 0 | 100 | 100 | 100 | 100 |
| 2 | 0 | 0 | 0 | 0 | 100 | 100 | 97 | 100 |

TABLE 2

Post-Emergence Herbicidal Activity
Application Rate: 27.5 micrograms/cm², unless otherwise noted

| | Broad-Leaf Plants % Phytotoxicity | | | | Grasses % Phytotoxicity | | | |
|---|---|---|---|---|---|---|---|---|
| Compound No. | Lambs-quarter | Mustard | Pig-weed | Soybean | Crab-grass | Water-grass | Wild Oats | Rice |
| 1 | 0 | 0 | 0 | 0 | 100 | 100 | 100 | 100 |

TABLE 2-continued

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 2 | 0 | 0 | 10 | 15 | 100 | 100 | 100 | 100 |

As can be seen from the above Tables the title compound of Example 1, exhibited excellent pre-emergence and post-emergence phytotoxicity against grasses and was completely selective to grasses.

Obviously, many modifications of the invention described hereinabove, and in the claims, can be made without departing from the essence and scope thereof.

What is claimed is:

1. A compound having the formula:

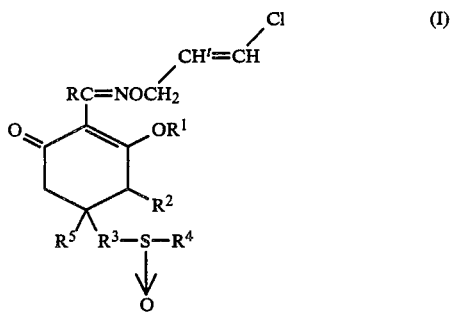

wherein R is lower alkyl;
R¹ is hydrogen, a compatible cation, or the group

wherein R⁶ is lower alkyl, phenyl, indenyl, naphthyl or benzyl;
R² is hydrogen carboxy or alkoxycarbonyl having 2 through 6 carbon atoms;
R³ is lower alkylene;
R⁴ is lower alkyl, phenyl or substituted phenyl having 1 through 3 substituents independently selected from the group of lower alkyl, lower alkoxy, halo and haloalkyl having 1 through 4 carbon atoms and 1 through 3 halo substituents independently selected from the group of fluoro, chloro, bromo or iodo;
R⁵ is hydrogen or lower alkyl; and the designation = indicates trans-orientation with the double bond.

2. The compound of claim 1 wherein R is n-propyl.
3. The compound of claim 1 wherein R¹ is hydrogen or a compatible cation.
4. The compound of claim 1 wherein R⁵ is hydrogen.
5. The compound of claim 1 wherein R³ is a branched chained alkylene group having 2 through 4 carbon atoms.
6. The compound of claim 5 wherein R⁴ is ethyl or propyl.
7. The compound of claim 1 wherein R⁴ is ethyl or propyl.
8. The compound of claim 1 wherein R¹ is the group

wherein R⁶ is as defined in claim 1.

9. The compound of claim 1 wherein R² is hydrogen.
10. The compound of claim 1 wherein R² is carboxy or alkoxycarbonyl having 2 through 6 carbon atoms.
11. The compound of claim 1 wherein the group —R³—S(O)—R⁴ is —CH₂CH(CH₃)—S(O)—CH₂CH₃.
12. The compound of claim 11 wherein R¹ is hydrogen or a compatible ion and R⁵ is hydrogen or methyl.
13. The compound of claim 12 wherein R⁵ is hydrogen, R is n-propyl, and R² is hydrogen.
14. The compound of claim 13 wherein R¹ is hydrogen.
15. The compound of claim 1 wehrein R⁴ is lower alkyl.
16. The compound of claim 1 wherein R⁴ is phenyl.
17. The compound of claim 1 wherein R⁴ is said substituted phenyl.
18. The compound of claim 17 wherein R⁴ is a monosubstituted phenyl.
19. The compound of claim 18 wherein R⁴ is 4-chlorophenyl.
20. The compound of claim 18 wherein R⁴ is 4-bromophenyl.
21. The compound of claim 17 wherein R⁴ is a disubstituted phenyl.
22. The compound of claim 21 wherein R⁴ is 2,6-dimethylphenyl.
23. A herbicidal composition comprising a herbicidally effective amount of a compound according to claim 1, or mixtures of such compounds, and a compatible carrier.
24. A herbicidal composition comprising a herbicidally effective amount of a compound according to claim 14, or mixtures thereof, and a compatible carrier.
25. A method for preventing or destroying grassy plants which comprises applying a herbicidally effective amount of a compound having the formula:

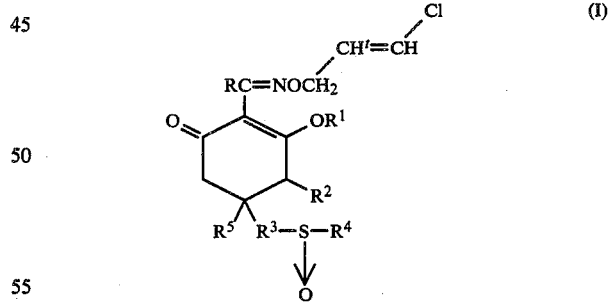

wherein R is lower alkyl;
R¹ is hydrogen, a compatible cation, or the group

wherein R⁶ is lower alkyl, phenyl, indenyl, naphthyl or benzyl;
R² is hydrogen carboxy or alkoxycarbonyl having 2 through 6 carbon atoms;
R³ is lower alkylene;

$R^4$ is lower alkyl, phenyl or substituted phenyl having 1 through 3 substituents independently selected from the group of lower alkyl, lower alkoxy, halo and haloalkyl having 1 through 4 carbon atoms and 1 through 3 halo substituents independently selected from the group of fluoro, chloro, bromo or iodo;

$R^5$ is hydrogen or lower alkyl; and the designation ═ indicates trans-orientation with the double bond; or mixtures thereof, to the foliage or potential growth medium of said plants.

26. A method for preventing or destroying grassy plants which comprises applying a herbicidally effective amount of a compound having the formula:

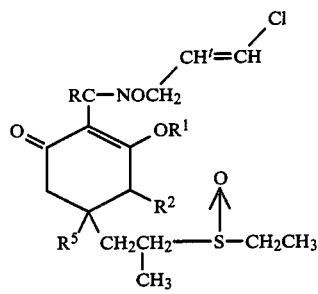

wherein R is propyl and $R^1$, $R^2$ and $R^5$ are each hydrogen; or mixtures thereof, to the foliage or potential growth medium of said plants.

* * * * *